United States Patent [19]
Frank et al.

[11] 4,193,979
[45] Mar. 18, 1980

[54] SODIUM 3-[[[2-(2-METHYL-5-NITRO-1H-IMIDAZOL-1-yl)ETHYL]-AMINO]CARBONYL]-2-PYRIDINECARBOXYLIC ACID AND RELATED COMPOUNDS LABELED WITH TECHNETIUM-99M

[75] Inventors: Patricia Frank, Evanston; Stephen Kraychy, Northbrook; Ernest F. LeVon, Evanston, all of Ill.

[73] Assignee: G. D. Searle & Co., Skokie, Ill.

[21] Appl. No.: 907,645

[22] Filed: May 22, 1978

[51] Int. Cl.² ............... C07D 401/12; A61K 43/00
[52] U.S. Cl. ..................... 424/1.5; 544/350; 546/5; 546/12; 546/278; 546/112
[58] Field of Search ..... 260/295 AM, 270 E, 270 PY; 424/1.5

[56] References Cited

U.S. PATENT DOCUMENTS

| 3,642,836 | 2/1972 | Cusic et al. | 260/281 |
| 3,770,763 | 11/1973 | Cusic et al. | 260/309 |
| 4,010,251 | 3/1977 | Green | 424/1.5 |

OTHER PUBLICATIONS

Vasa et al., Chem. Abs. 70, 37896t (1968).

Primary Examiner—Mark L. Berch
Attorney, Agent, or Firm—James R. Henes

[57] ABSTRACT

Sodium 3-[[[2-(2-methyl-5-nitro-1H-imidazol-1-yl)ethyl]-amino]carbonyl]-2-pyridinecarboxylic acid and related compounds which are labeled with radioactive technetium-99m are described as well as their preparations. These novel complexes are useful by reason of their utility as radiopharmaceutical imaging agents. Particularly, these complexes are useful as gallbladder and liver imaging agents.

15 Claims, No Drawings

SODIUM 3-[[[2-(2-METHYL-5-NITRO-1H-IMIDAZOL-1-yl)ETHYL]-AMINO]CARBONYL]-2-PYRIDINECARBOXYLIC ACID AND RELATED COMPOUNDS LABELED WITH TECHNETIUM-99M

It has been found in the art that complexes between certain types of organic compounds and radionuclides possess utility as radioagents useful as organ imaging agents. The requirements for radioagents suitable for the practice of this utility are stringent. These agents must be free of bacterial contaminants, pyrogens and pharmacological, antigenic or undesired radiation effects after adminstration. They must be labeled with a radionuclide possessing a principal gamma emission from 20 to 510 KeV to be detected by collimated NaI(Tl) crystals. However, if the scintillation cameras and scanning cameras are used, the radionuclide must possess a somewhat narrower gamma-energy range of about 70-400KeV. Nuclides with physical half lives from several hours to a few days and without beta emissions are most suitable for this utility. Lastly the radiopharmaceutical must be specific as to allow the external imaging of only the desired organ.

It is an object of the present invention to provide a radioagent encompassing all of the above-mentioned requirements. It is a further object of this invention to provide a method of external imaging utilizing said agent. It is still a further object of this invention to provide a method for the preparation of said agent.

The above objects are achieved by providing a radiolabeled diagnostic agent which combines the high target organ specificity of various drugs and biochemicals with the excellent nuclear imaging properties of the radioisotope technetium-99m. Other radioisotopes suitable for the practice of this invention are cobalt-57, gallium-68, gallium 67, indium-111 and indium-113m.

The invention is predicated on the discovery that chelates of technetium-99m with 3-[[[2-(2-methyl-5-nitro-1H-imidazol-1-yl)ethyl]-amino]carbonyl]-2-pyridinecarboxylic acid and related compounds such as their corresponding sodium and lithium salts have a high degree of in vivo stability, are highly specific to certain organs and, additionally, possess excellent nuclear imaging properties.

The above chelates are prepared by reacting technetium-99m with the chelating agent.

Technetium-99m is commercially available either from an isotope generator as a daughter product of molybdenum-99 or as a direct product from a commercial supplier. It is also available as a solvent extraction product from molybdenum-99 solutions generally as alkali metal pertechnetate solutions at 5–100 mCi/ml. A further discussion of preparative methods appears in U.S. Pat. Nos. 3,468,808 and 3,382,152.

The technetium-99m chelate is most preferably prepared by reducing a solution of a pertechnetate, e.g., an alkali metal pertechnetate in the presence of the chelating agent. The reduction is preferably effected utilizing stannous chloride as a reducing agent. Any suitable reducing agent may be employed including other stannous salts such as stannous acetate, stannous tartrate, stannous oxalate as well as cuprous salts or ferrous salts. As a result of this reduction step, the product may contain a significant proportion of a tin chelate. It is to be understood that the present invention includes the product mixture containing both the radiometal chelate and the corresponding tin chelate.

Indeed, the composition of the invention is most conveniently provided as a sterile kit consisting of nonradioactive chemicals for mixing with the radiometal source prior to use. The kit preferably contains a stannous salt solution, pH buffer solution or combinations thereof. Using sterile reagents and aseptic techniques, the respective solutions would be mixed with each other in any desired order and then with the radiometal source solution. The resulting solution containing the radiometal chelate, the tin chelate and the excess chelating agent may then be employed directly for imaging purposes.

Generally, a solution adapted for intravenous administration containing up to 15mCi of radioactivity is administered to the patient. Generally, this may be accomplished by administering 0.2–1 ml of a solution containing from about 0.1 to about 50 mg of chelating agent. Radioassay of the radio-isotope in the desired organ may be accomplished utilizing conventional equipment, such as a scintillation camera, etc.

Organ specificity is determined by the particular chelating agent employed. The chelates according to the present invention are cleared through the liver and gallbladder. Therefore, the chelates of the present invention may be utilized as radiopharmaceutical diagnostic agent for gallbladder imaging e.g. demonstration of bile duct patency, and an agent for use in liver function studies.

The chelating agents of the present invention are compounds of the general formula

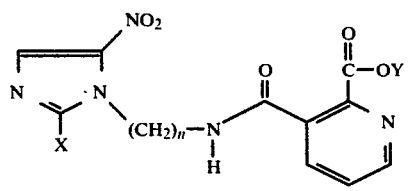

wherein X can be H or alkyl having 1 to 4 carbon atoms; Y is hydrogen or the cation of a pharmaceutically acceptable salt; and n is a positive integer from 2 to 4.

Also within the scope of the present invention is a chelating agent of the formula

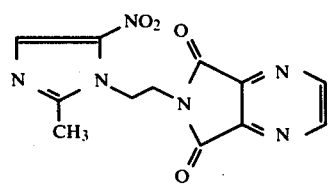

It has been found that a chelating agent of the above formula when labeled with a suitable radioisotope also possesses utility as an imaging agent.

Preferred embodiments of the chelating agents of the present invention are compounds of the general formula

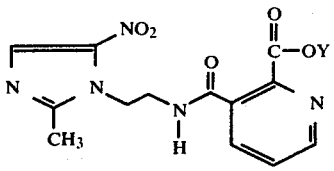

wherein Y is hydrogen or sodium or lithium.

The most preferred chelating agents of the present invention are 3-[[[2-(2-methyl-5-nitro-1H-imidazol-1-yl)ethyl]amino]carbonyl]-2-pyridinecarboxylic acid; 3-[[[2-(2-methyl-5-nitro-1H-imidazol-1-yl)ethyl]amino]carbonyl]-2-pyridinecarboxylic acid sodium salt; and 3-[[[2-methyl-5-nitro-1H-imidazol-1-yl)ethyl]amino]carbonyl]-2-pyridinecarboxylic acid, lithium salt.

A representative compound of the present invention 3-[[[2-(2-methyl-5-nitro-1H-imidazol-1-yl)ethyl]amino]carbonyl]-2-pyridinecarboxylic acid, sodium salt, hydrate (3:2) labeled with technetium-99m is seen to localize in the gallbladder of normal dogs and monkeys. In order to assess the potential of this radiopharmaceutical drug for diagnostic use, dogs and monkeys were injected intravenously with 3-[[[2-(2-methyl-5-nitro-1H-imidazol-1yl)ethyl]amino]carbonyl]-2-pyridinecarboxylic acid, sodium salt, hydrate (3:2) labeled with technetium-99m. The distribution of radioactivity in each animal was determined using a large field of view scintillation camera. In addition, the radioactivity in the gallbladder and the liver in selected animals was analyzed quantitatively using computer methodology.

METHOD

A fasted and tranquilized laboratory dog is given between 1 and 1.5 mCi of the technetium-99m complex of Example 6 via either the saphenous or cephalic vein using a 1 cc tuberculin syringe and #25-1 needle and then is positioned under the gamma camera. Imaging takes place for 3 hours. A 20% technetium-99m window and a 140KEV high resolution converging collimator are used. Approximately 300,000–400,000 counts are accumulated on both video tape and self-developing film in the full ventral position.

Pictures are examined for concentration of radioactivity in the gallbladder, clearance of the radioactive material from the liver and normal size and shape of the gallbladder. Video tape is processed by computer for quantification of radioactivity in the gallbladder and liver.

Essentially equivalent techniques are used to image the gallbladder of the monkey.

Images of a dog injected intravenously with a representative compound of the present invention—3[[[2-(2-methyl-5-nitro-1H-imidazol-1-yl)ethyl]amino]carbonyl]-2-pyridinecarboxylic acid, sodium salt, hydrate (3:2) labeled with technetium-99m were taken at 30, 90 and 180 minutes post injection.

The image at 30 minutes post injection shows radioactivity in the gallbladder with some still in the bile ducts and a small amount diffusely distributed in the liver. Radioactivity is also seen in the urinary bladder.

The image at 90 minutes post injection shows almost all of the radioactivity to be in the gallbladder or urinary bladder.

The image at 180 minutes post injection is the same as at 90 minutes post injection except that a small amount of radioactivity is seen in the gastrointestinal tract.

Images of 3-[[[2-(2-methyl-5-nitro-1H-imidazol-1-yl)ethyl]amino]carbonyl]-2-pyridinecarboxylic acid, sodium salt, hydrate (3:2) labeled with technetium-99m in the monkey are essentially the same except more radioactivity is seen in the gastrointestinal tract. In addition, the radioactivity enters the gastrointestinal tract sooner after injection of the labeled compound than was seen in the dog.

Rhesus monkeys were chosen for computer analysis. The analysis showed small, moderate and large amounts of radioactivity leaving the gallbladder and entering the small intestine. The analysis demonstrates the ratios of gallbladder and liver radioactivity to background radioactivity in these animals. Liver ratios ranged from 20:1 to 10:1 throughout the 180 minute studies, while gallbladder ratios reached a maximum of from 150:1 to 200:1. Maximum gallbladder to background ratios were reached as in the dog at about 90 to 120 minutes post injection. Liver ratios remained at the same level from 15 to 180 minutes.

In each animal injected with 3-[[[2-(2-methyl-5-nitro-1H-imidazol-1-yl)ethyl]amino]carbonyl]-2-pyridinecarboxylic acid, sodium salt, hydrate (3:2) labeled with technetium-99m, radioactivity was filtered from the blood by the liver and collected in the biliary tract and gallbladder. In all monkeys this radioactivity emptied from the gallbladder into the duodenum within the time frame of the study.

Analysis of the ratio of gallbladder and liver to background in dogs receiving 3-[[[2-(2-methyl-5-nitro-1H-imidazol-1-yl)ethyl]amino]carbonyl]-2-pyridinecarboxylic acid sodium salt, hydrate (3:2) labeled with technetium-99m reveal that ratios of 12:1 for liver to background and 175:1 to 220:1 for gallbladder to background were achieved. Maximum ratios were observed at 90 to 105 minutes post injection of the compound. The density ratios for gallbladder were very similar in two dogs.

For the practice of this invention 3-[[[2-(2-methyl-5-nitro-1H-imidazol-1-yl)ethyl]amino]carbonyl]-2-pyridinecarboxylic acid, lithium salt labeled with technetium-99m is considered to be equivalent to 3-[[[2-(2-methyl-5-nitro-1H-imidazol-1-yl)ethyl]amino]carbonyl]-2-pyridinecarboxylic acid, sodium salt, hydrate (3:2) labeled with technetium-99m.

The following examples are presented to further illustrate the present invention; they should not be construed as limiting it in spirit or in scope. In these examples, quantities are indicated in parts by weight unless parts by volume are specified, and temperatures are indicated in degrees centigrade (°C). The relationship between parts by weight and parts by volume is the same as that existing between grams and milliliters.

EXAMPLE 1

To a solution of 5.0 parts by weight of quinolinimide in 50 parts by volume of N,N-dimethylformamide is added 2.0 parts by weight of potassium hydroxide granules. The mixture is heated on a steam bath and 15 parts by volume of methanol is added to dissolve the potassium hydroxide. The mixture is then diluted with 50 parts by weight of additional N,N-dimethylformamide and the solution is heated under reduced pressure to remove the methanol. To the resulting N,N-dimethylformamide solution is added a solution of 10.0 parts by weight of 1-(2-hydroxyethyl)-2-methyl-5-nitroimidazole tosylate in 95 parts by volume of N,N-dimethylformamide. The resulting yellow solution is heated on a steam bath for 1 hour and the solvent is then evaporated under reduced pressure to leave a solid residue. This residue is triturated with 435 parts of toluene and the insoluble material is separated by filtration. The solid is mixed with 200 parts by volume of water and the insoluble material is separated by filtration and dried to give N-[2-(2-methyl-5-nitro-1-imidazolyl)ethyl]quinolinimide. N-[2-(2-methyl-5-nitro-1-imidazolyl)ethyl]quinolinimide is purified by dissolving 1 part by weight in 10 parts by volume of N,N-dimethylformamide at 70° C. followed by dilution with 20 parts by volume of ethanol. The resulting product is filtered, washed with ethanol and dried to afford N-[2-(2-methyl-5-nitro-1-imidazolyl)ethyl]quinolinimide, melting at 218°-220° C. This compound is represented by the following formula

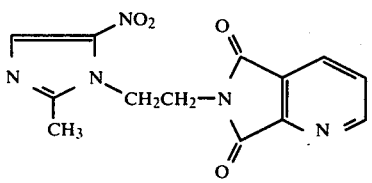

This procedure is also described in U.S. Pat. No. 3,642,836.

EXAMPLE 2

To a stirred solution of 44.5 parts by volume of a 5.46% aqueous potassium hydroxide solution is added 13.0 parts by weight of N-[2-(2-methyl-5-nitro-1H-imidazolyl)ethyl]quinolinimide. The resulting mixture is stirred at room temperature for 0.5 hour (or until most is dissolved) and then filtered to remove insoluble material. Evaporation of the filtrate affords a gum. This gum is taken-up in 25 parts by volume of warm methanol. Seeding of this methanolic solution affords a crystalline product which is separated and again dissolved in 250 parts by volume of warm methanol. The methanolic solution is then treated with activated charcoal, filtered and concentrated to a 100 parts by volume. Seeding of the solution affords a crystalline product which is separated by filtration and then dried in vacuo to afford 2-[[[2-(2-methyl-5-nitro-1H-imidazol-1-yl)ethyl]amino]carbonyl]-3-pyridinecarboxylic acid, potassium salt, decomposing at 270° C. This compound is represented by the following structural formula

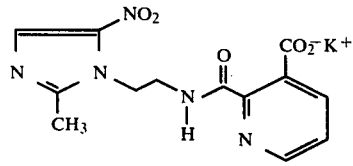

EXAMPLE 3

Evaporation of the methanolic mother liquor from the preparation of crude 2-[[[2-(2-methyl-5-nitro-1H-imidazol-1-yl)ethyl]amino]carbonyl]-3-pyridinecarboxylic acid, potassium salt (Example 2) affords a gum. This gum is dissolved in 25 parts by volume of distilled water and then the aqueous solution is acidified with glacial acetic acid, scratching of the glass container which contained the solution induces the crystallization of the product. The product is filtered from the solvent, washed with water and dried to afford 3-[[[2-(2-methyl-5-nitro-1H-imidazol-1-yl)ethyl]amino]carbonyl]-2-pyridinecarboxylic acid which melts with decomposition at 167°-169° C. This compound is represented by the following structural formula

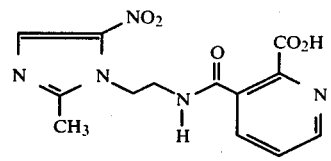

EXAMPLE 4

0.958 Part by weight of 3-[[[2-(2-methyl-5-nitro-1H-imidazole-1-yl)ethyl]amino]carbonyl]-2-pyridinecarboxylic acid is taken up in 3.0 parts by volume of a 4.00% solution of aqueous sodium hydroxide. The resulting solution is then filtered. Evaporation of the filtrate affords a gum. This gum is dissolved in methanol. The methanolic solution is then treated with activated charcoal, filtered and evaporated to afford a residue. The resulting residue is taken-up in 10 parts by volume of methanol. This methanolic solution is diluted with 25 parts by volume of a 1:1 methanol/ethyl ether solution and then added to a stirred solution of ethyl ether. The resulting precipitate is filtered, washed with ethyl ether and dried in vacuo to afford a gum. This gum is again dissolved in methanol. The methanolic solution is again treated with activated charcoal, filtered and evaporated to afford a residue. This residue is taken-up in a 1:1 methanol/ethyl ether solution, and precipitated by slow addition to excess ethyl ether. The resulting precipitate is separated and then dried in vacuo to afford 3-[[[2-(2-methyl-5-nitro-1H-imidazol-1-yl)ethyl]amino]carbonyl]-2-pyridinecarboxylic acid, sodium salt, hydrate (3:2) as an amorphous powder.

EXAMPLE 5

1.0 Parts by weight of 3-[[[2-methyl-5-nitro-1H-imidazol-1-yl)ethyl]amino]carbonyl]-2-pyridinecarboxylic acid is taken-up in 3.1 parts by volume of 1.0 N aqueous lithium hydroxide solution and about 2 parts by volumes of methanol. Evaporation of the resulting solution affords a residue. This residue is then taken-up in 30.0 parts by volume of methanol. The methanolic solution is then concentrated to a lower volume. Seeding of the solution affords 3-[[[2-(2-methyl-5-nitro-1H-imidazol-1-yl)ethyl]amino]carbonyl]-2-pyridinecarboxylic acid, lithium salt.

EXAMPLE 6

0.004 to 0.024 Parts by weight of 3-[[[2-methyl-5-nitro-1H-imidazol-1-yl)ethyl]amino]carbonyl]-2-pyridinecarboxylic acid, sodium salt, hydrate (3:2) which was prepared according to Example 4 is dissolved in 2.5-4.0 parts by volume of sodium $^{99m}$Tc-pertechnetate solution in normal saline (0.9% sodium chloride solution) containing 1638 mCi of $^{99m}$Tc obtained from a commercial generator. To this solution is added 25λ (microliters) of a stannous chloride/hydrochloric acid solution which is prepared by dissolving 0.040 parts by weight of stannous chloride in 1.0 parts by volume of a 1 N aqueous hydrochloric acid. The pH of this solution is then adjusted to approximately 5.5 by the addition of 0.1 N aqueous sodium hydroxide solution.

After completion of the complex formation—optimum time being 45 minutes—an aliquot is analyzed by thin layer chromatography using thin layer chromatography sheets of silica gel and acetone as the developing solvent. The chromatogram is then analyzed by means of a radioactive scanning instrument and an electronic integrator. Unreduced "free" pertechnetate is located at or very near to the solvent front and is present in 0–6% yield, usually 0–2%. Reduced pertechnetate and/or the product complex is present at the origin to the extent of 94–100% yield.

Simultaneously a second aliquot, containing 500–1600 microcuries is analyzed by polyacrylamide gel chromatography using a 0.7×20 cm. column of a suitable gel and normal saline (0.9% sodium chloride solution) as the eluent. Twenty to forty, one-milliliter fractions are collected and the radioactivity of each fraction is determined by means of a dose calibrator or gamma counter. The labeled product is eluted in fractions three to twenty in 86–93% yield.

EXAMPLE 7

0.002–0.024 Parts by weight of 3-[[[2-methyl-5-nitro-1H-imidazol-1-yl)ethyl]amino]carbonyl]-2-pyridinecarboxylic acid, sodium salt, hydrate (3:2) which was prepared according to Example 4 is dissolved in a minimum amount of water (0.05 ml. per mg.). To this resulting solution is added 0.2 to 0.6 parts by volume of a stannous chloride/hydrochloric acid solution which was prepared by dissolving 0.040 parts by weight of stannous chloride dihydrate in 1.0 parts by volume of a 1 N aqueous hydrochloric acid and enough distilled water (nitrogen-purged distilled water) to bring the volume up to 50 parts by volume. The pH of the mixture is then adjusted to 5–6 by the addition of 0.1 N sodium hydroxide solution. Sodium pertechnetate solution in normal saline (0.9% sodium chloride solution) containing 5–50 mCi is then added to this mixture.

After completion of the complex formation (optimum time being 45 minutes) the solution is analyzed in the same manner as described in Example 6.

EXAMPLE 8

0.024 Parts by weight of N-[2-(2-methyl-5-nitro-1-imidazolyl)ethyl]quinolinimide is dissolved in 0.700 parts by volume of a 0.1 N sodium hydroxide solution. To the resulting solution is added 0.500 parts by volume of a stannous chloride-hydrochloric acid solution which is prepared by dissolving 0.040 parts by weight of stannous chloride dihydrate in 1.00 parts by volume of a 1 N aqueous hydrochloric acid and then adding enough distilled water to bring the volume up to 50 parts by volume. The pH of the mixture is then adjusted to approximately 5 by the addition of 0.1 N sodium hydroxide and 0.1 N hydrochloric acid as required. 2.0 Parts by volume of sodium pertechnetate solution in normal saline (0.9% sodium chloride solution) containing approximately 20 mCi of $^{99m}$Tc is then added and the resulting solution is allowed to stand for 15 minutes. Analysis by TLC (procedure described in Example 6) indicated 99% reduction of pertechnetate and by polyacrylamide gel chromatography (procedure described in Example 6) 96.5% radiochemical yield of desired complex. Thus the mixture of salts obtained on direct hydrolysis of the imide contains 3-[[[2-(2-methyl-5-nitro-1H-imidazol-1-yl)ethyl]amino]carbonyl]-2-pyridinecarboxylic acid, sodium salt. In this mixture it shows radiopharmaceutical properties similar to the purified material which was used example 7.

EXAMPLE 9

To a solution of 1.80 parts by weight of 2,3-pyrazinedicarboximide which was prepared according to the procedure described in Helvetica *Chemica Acta* 41 (1958) p. 512 in 40 parts by volume of dry dimethylformamide is added 17.0 parts by volume of methanol containing 0.85 parts by weight of potassium hydroxide pellets. The combination of these two solutions results in the formation of a precipitate. To this mixture is then added in one portion a slightly warm solution of 3.01 parts by weight of 1-(2-hydroxyethyl)-2-methyl-5-nitroimidazole methanesulfonate (preparation of 1-(2-hydroxyethyl)-2-methyl-5-nitroimidazolemethanesulfonate is described in U.S. Pat. No. 3,770,763) in 40.0 parts by volume of dimethylformamide. The mixture turns dark blue in color, then upon swirling turns green in color and eventually turns yellow in color. The mixture is then heated on a steam bath for 4 hours at an internal temperature of 70°–85° C. After cooling, the mixture to room temperature the insoluble material is separated by filtration, rinsed with dimethylformamide and air dried. The mother liquor is rinsed into a round bottom flask, concentrated to a volume of about 40 parts, then diluted to a volume of 100 parts with water and allowed to stand overnight. The resulting solid material which separates out of this liquor is separated by filtration, washed with water and air dried to afford a product, in the form of brown needles, melting at 231°–234° C. This product is then taken up in 8.0 parts by volume of warm dimethylformamide; activated carbon is added to the solution and the solution is then filtered. The filtrate is diluted with 20 parts by volume of water and then seeded. The resulting crystals are separated by filtration, washed with methanol and air dried to afford 6-[2-(2-methyl-5-nitro-1H-imidazole-1-yl)ethyl]-5H-pyrrolo[3,4-b]pyrazine-5,7(6H-dione), melting at 232°–234° C. This compound is represented by the following structural formula

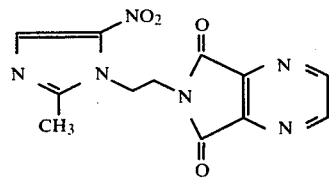

EXAMPLE 10

0.0127 Parts by weight of 6-[2-(2-methyl-5-nitro-1H-imidazol-1-yl)ethyl]-5H-pyrrolo[3,4-b]pyrazine-5,7(6H)-dione is dissolved in 1.0 parts by volume of a 1 N sodium hydroxide solution with heating. To 2.0 parts by volume of sodium pertechnetate solution in normal saline (0.9% sodium chloride solution) containing approximately 40 mCi of $^{99m}$Tc is added 20 μl of a stannous chloride-hydrochloric acid solution which is prepared by dissolving 0.050 parts by weight of stannous chloride dihydrate in 1.00 parts by volume of a 1 N aqueous hydrochloric acid. After 15 minutes the solution containing 6-[2-(2-methyl-5-nitro-1H-imidazol-1-yl)ethyl]-5H-pyrrolo[3,4-b]pyrazine-5,7(6H)-dione is added and the pH of the mixture is adjusted to approximately 9.7 by the addition of 0.1 N sodium hydroxide and 0.1 N hydrochloric acid as required. The resulting solution is heated to boiling and then allowed to stand at room temperature. Analysis by TLC (procedure described in Example 6) indicated 90% reduction of pertechnetate and by polyacrylamide gel chromatography (procedure described in Example 6) 44% radiochemical yield of desired complex.

What we claim is:

1. A compound of the formula

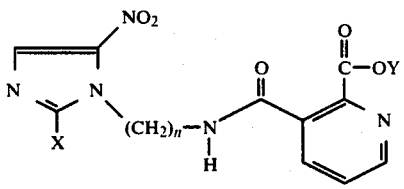

wherein X can be an alkyl having 1 to 4 carbon atoms; Y is hydrogen or the cation of a pharmaceutically acceptable salt and n is a positive integer from 2 to 4.

2. A chelate of technetium-99m and a compound of the formula

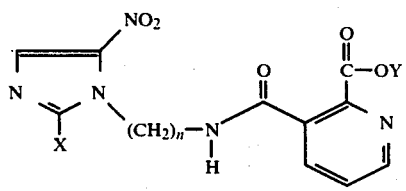

wherein X can be an alkyl having 1 to 4 carbon atoms; Y is hydrogen or the cation of a pharmaceutically acceptable salt; and n is a positive integer from 2 to 4.

3. A chelate of technetium-99m and a compound of the formula

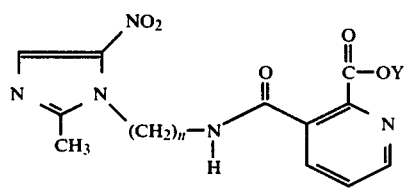

wherein Y is hydrogen or the cation of a pharmaceutically acceptable salt and n is a positive integer from 2 to 4.

4. A chelate, according to claim 2, of technetium-99m and a compound of the formula

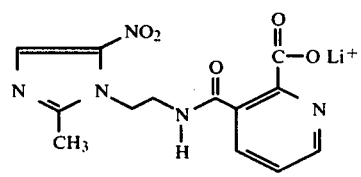

5. A chelate, according to claim 2, of technetium-99m and a compound of the formula

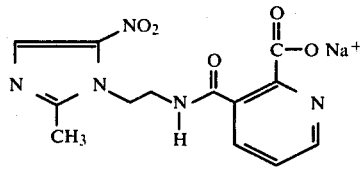

6. A composition for gall bladder imaging consisting essentially of an effective amount of a mixture of technetium-99m chelate of claim 2 and the tin chelate of said chelating agent in aqueous solution.

7. A composition, according to claim 6, consisting essentially of a mixture of technetium-99m chelate of 3-[[[2-(2-methyl-5-nitro-1H-imidazol-1-yl)ethyl]amino]carbonyl]-2-pyridinecarboxylic acid, lithium salt and the tin chelate of 3-[[[2-(2-methyl-5-nitro-1H-imidazol-1-yl)ethyl]amino]carbonyl]-2-pyridinecarboxylic acid, lithium salt in aqueous solution.

8. A composition, according to claim 6, consisting essentially of a mixture of technetium-99m chelate of 3-[[[2-(2-methyl-5-nitro-1H-imidazol-1-yl)ethyl]amino]carbonyl]-2-pyridinecarboxylic acid, sodium salt, hydrate (3:2 and the tin chelate of 3-[[[-(2-methyl-5-nitro-1H-imidazol-1-yl)ethyl]amino]carbonyl]-2-pyridinecarboxylic acid, sodium salt, hydrate (3:2) in aqueous solution.

9. A composition for gall bladder imaging consisting essentially of an effective amount of a mixture of the technetium-99m chelate of claim 2, the tin chelate of said chelating agent and said chelating agent in aqueous solution.

10. A composition according to claim 9, consisting essentially of a mixture of the technetium-99m chelate of 3[[[2-(2-methyl-5-nitro-1H-imidazol-1-yl)ethyl]amino]carbonyl]-2-pyridinecarboxylic acid, lithium salt, the tin chelate 3-[[[2-(2-methyl-5-nitro-1H-imidazol-1-yl)ethyl]amino]carbonyl]-2-pyridinecarboxylic acid, lithium salt and 3-[[[2-(2-methyl-5-nitro-1H-imidazol-1-yl)ethyl]amino]carbonyl]-2-pyridinecarboxylic acid, lithium salt in aqueous solution.

11. A composition, according to claim 9, consisting essentially of a mixture of the technetium-99m chelate of 3-[[[2-(2-methyl-5-nitro-1H-imidazol-1-yl)ethyl]amino]carbonyl]-2-pyridinecarboxylic acid, sodium salt, hydrate (3:2), the tin chelate of 3-[[[2-(2-methyl-5-nitro-1H-imidazol-1-yl)ethyl]amino]carbonyl]-2-pyridinecarboxylic acid, sodium salt, hydrate (3:2) and 3-[[[2-(2-methyl-5-nitro-1H-imidazol-1-yl)ethyl]amino]carbonyl]-2-pyridinecarboxylic acid, sodium salt, hydrate (3:2) in aqueous solution.

12. A method of gallbladder imaging which comprises the intravenous administration of a solution containing the chleate of claim 2.

13. A compound according to claim 1 of the formula

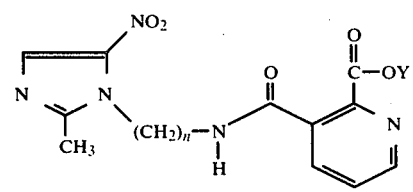

wherein Y is hydrogen or the cation of a pharmaceutically acceptable salt and n is a positive integer from 2 to 4.

14. A compound, according to claim 1, which is 3-[[[2-(2-methyl-5-nitro-1H-imidazol-1-yl)ethyl]amino]carbonyl]-2-pyridinecarboxylic acid, lithium salt.

15. A compound, according to claim 1, which is 3-[[[2-(2-methyl-5-nitro-1H-imidazol-1-yl)ethyl]amino]carbonyl]-2-pyridinecarboxylic acid, sodium salt, hydrate (3:2).

* * * * *